United States Patent
Shi et al.

(10) Patent No.: US 10,761,026 B2
(45) Date of Patent: *Sep. 1, 2020

(54) METHODS TO QUANTIFY AN ION IN A DENTAL BIOFILM

(71) Applicant: The Procter & Gamble Company, Cincinnati, OH (US)

(72) Inventors: Yunming Shi, Beijing (CN); Swapna Basa, Beijing (CN); Ross Strand, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/910,759

(22) Filed: Mar. 2, 2018

(65) Prior Publication Data

US 2018/0252644 A1     Sep. 6, 2018

(30) Foreign Application Priority Data

Mar. 3, 2017   (WO) .......................... CN2017/075537

(51) Int. Cl.
| | | |
|---|---|---|
| *G01N 21/64* | (2006.01) | |
| *A61K 8/21* | (2006.01) | |
| *C12Q 1/04* | (2006.01) | |
| *A61K 8/41* | (2006.01) | |
| *A61Q 11/00* | (2006.01) | |
| *A61B 5/00* | (2006.01) | |
| *A61C 19/04* | (2006.01) | |
| *A61K 8/27* | (2006.01) | |
| *A61K 8/19* | (2006.01) | |
| *G02B 21/00* | (2006.01) | |

(52) U.S. Cl.
CPC ....... *G01N 21/6428* (2013.01); *A61B 5/0071* (2013.01); *A61B 5/0088* (2013.01); *A61B 5/4848* (2013.01); *A61B 5/682* (2013.01); *A61C 19/04* (2013.01); *A61K 8/19* (2013.01); *A61K 8/21* (2013.01); *A61K 8/27* (2013.01); *A61K 8/416* (2013.01); *A61Q 11/00* (2013.01); *C12Q 1/04* (2013.01); *G01N 21/6458* (2013.01); *G01N 21/6486* (2013.01); *A61K 2800/434* (2013.01); *A61K 2800/58* (2013.01); *G02B 21/0076* (2013.01)

(58) Field of Classification Search
CPC ................................................... A61B 5/0071
See application file for complete search history.

(56) References Cited

U.S. PATENT DOCUMENTS

| | | | |
|---|---|---|---|
| 3,935,305 | A | 1/1976 | Delaney et al. |
| 6,309,835 | B1 | 10/2001 | Iyer et al. |
| 8,283,135 | B2 | 10/2012 | Doyle et al. |
| 8,926,951 | B2 | 1/2015 | Ratcliff et al. |
| 9,682,023 | B2 | 6/2017 | Ratcliff et al. |
| 10,280,444 | B2 | 5/2019 | Shi |
| 2007/0053849 | A1 | 3/2007 | Doyle et al. |
| 2015/0297478 | A1 | 10/2015 | Ratcliff et al. |

FOREIGN PATENT DOCUMENTS

| | | |
|---|---|---|
| JP | 2010122110 | 6/2010 |
| WO | WO2016172334 | 10/2016 |
| WO | WO2017000837 | 1/2017 |

OTHER PUBLICATIONS

Yang et al. Applied and Environmental Microbiology, 2006, 6734-6742.*
Lan et al., The Royal Society of Chemistry, 2014, 139:5223-5229.*
Mei et al., Materials, 2016, 9, pp. 1-12 as printed.*
Hans-Curt Flemming, Thomas R. Neu and Daniel J. Wozniak, The EPS Matrix: The "House of Biofilm Cells", Journal of Bacteriology Nov. 2007, vol. 189 No. 22, pp. 7945-7947.
Adav S S et al: "Stereological assessment of extracellular polymeric substances, exo-enzymes, and specific bacterial strains in bioaggregates using fluorescence experiments", Biotechnology Advances, Elsevier 1 Publishing, Barking, GB, vol. 28, No. 2, Mar. 1, 2010 (Mar. 1, 2010), pp. 255-280, XP026872199, ISSN: 0734-9750 [retrieved on Jan. 6, 2010].
PCT/CN2017/075537 PCT Search Report, dated Jun. 26, 2019, 10 pages.
S R Wood' et al: "Architecture of Intact Natural Human PlaqueBiofilms Studied by Confocal Laser Scanning MicroscopyIntroduction", J Dent Res, Jan. 1, 2000, pp. 21-27, XP055590836,Retrieved from the Internet: URL:https://journals.sagepub.com/doi/pdf/10.1177/00220345000790010201.
Tong Zhang et al: "Quantification of extracellular polymericsubstances in biofilms by confocal laser scanning microscopy", Biotechnology Letters, Mar. 1, 2001, pp. 405-409, XP055590815,DordrechtDOI: 10.1023/A:1005620730265Retrieved from the Internet:URL:https://link.springer.com/content/pdf/10.1023/A:1005620730265.pdf.

\* cited by examiner

*Primary Examiner* — Bin Shen

(74) *Attorney, Agent, or Firm* — Jason J. Camp

(57) ABSTRACT

A method of quantitating of ions in the extracellular polymer substances area of a dental biofilm is an effective way of assessing efficacy of oral care compositions.

17 Claims, 4 Drawing Sheets

METHODS TO QUANTIFY AN ION IN A DENTAL BIOFILM

FIELD OF THE INVENTION

The present disclosure is directed to methods for quantifying one or more ions in a dental biofilm.

BACKGROUND OF THE INVENTION

Dental plaque is an example of bacterial biofilm. Dental plaque is generally made up of bacteria and extracellular polymer substances (so called "EPS"). EPS are biopolymers of microbial origin in which biofilm microorganisms are embedded. *The EPS Matrix: The "House of Biofilm Cells"*, Hans-Curt Flemming, Thomas R. Neu and Daniel J. Wozniak *J. Bacteriol.* 2007, 189(22):7945. Dental plaque forms tartar and is associated with oral diseases such as caries and periodontal disease (e.g., gingivitis and periodontitis). Dental plaque can give rise to dental caries caused by the acid from the bacterial degradation of fermentable sugar. Therefore, dental plaque control and removal is important and the objective of many oral care compositions and regimens. Therefore, there is generally a continuing need to further understand the mechanisms of dental plaque formation and design oral care compositions that control or remove dental plaque.

Methods for quantitating the efficacy of oral care compositions (e.g., toothpaste, mouthwash etc.) at dislodging cells from biofilm test surfaces or inhibiting or delaying the accumulation of cells on a test surface have generally been described. Also, fluorescent probes, and confocal laser scanning microscopy (CLSM), have been generally used to assess ions and bacterial vitality of biofilm.

The role of ions in biofilm as well as use of certain ions in oral healthcare is a subject of ongoing study. Ions could inherently exist or be introduced in biofilm. For example, biofilm naturally contains calcium ions. There are abundant calcium ions ($Ca^{2+}$) in dental plaque, and the amount of calcium in plaque is two to three times greater than in saliva. It is believed that positively charged calcium ions in the saliva mask the negative charges between bacteria and a tooth's surface allowing the bacteria to attach and multiply on the tooth surface, thus contributing to the formation of dental plaque. Accordingly, inhibiting the role of calcium in biofilm has been a target of therapeutic focus in some oral care compositions. Certain ions have been added to oral care compositions to help prevent dental plaque and oral disease. For example, cetylpyridinium chloride (CPC), stannous ($Sn^{2+}$), silver ($Ag^+$), copper ($Cu^{2+}$) and zinc ($Zn^{2+}$) are reported to help inhibit certain bacteria that can lead to tooth decay in human interproximal dental plaque. Fluoride (F−) is an ion found to help prevent caries.

It is reported that it is often difficult to purify EPS matrix constituent apart from other components of the biofilm such as cells. *J. Bacteriol.* 2007, 189(22):7945. However, there is a need for methods at quantitating ions localized in the EPS area of dental biofilm. For example, it is believed that calcium ions act as a "glue" or "scaffold" of EPS components. Other ions, such as stannous, zinc, fluoride could be released (or the release can be optimized) from oral care compositions to the EPS portion of dental biofilm to deliver increased efficacy. Inside cell clusters the locally high cell densities and the presence of EPS arrest the flow of water. Diffusion is limited in these biofilm systems because fluid flow is reduced and the diffusion distance is increased in the dental biofilm. As most pathogenic anaerobic microbes that cause gum problems typically reside in inner layer of EPS, these aforementioned ions need to diffuse deeper to treat these microbes. Accordingly there is a need for methods to study the diffusion pattern of these ions in the EPS area of dental biofilm.

SUMMARY OF THE INVENTION

The present invention addresses at least one of these needs by providing a method of quantitating ions within the extracellular polymer substances ("EPS") area of dental biofilm. The present invention is based, in part, on the surprising use of EPS fluorescent probes that are specific for EPS of dental biofilm. It is the combination of EPS fluorescent probes coupled with one or more ion fluorescent probes that enables the quantification of ions in the EPS area of dental biofilm. Accordingly, one aspect of the invention provides a method of quantitating an ion within an extracellular polymer substances ("EPS") area of dental biofilm comprising the steps: optionally treating, preferably treating, the dental biofilm with an oral care composition; labeling the optionally treated dental biofilm with an EPS fluorescent probe; labeling the optionally treated dental biofilm with an ion fluorescent probe; defining an EPS area of the dental biofilm by measuring fluorescent light emitted from the labeled EPS biofilm; and quantitating the ion by measuring fluorescence light emitted from the labeled ion within the defined EPS area of the biofilm. Preferably the oral care composition is selected from the group consisting of dentifrice, toothpaste, mouthwash, gel, leave-on gel, and combinations thereof. Preferably an ion from the ion source is selected from the group consisting of calcium, stannous, zinc, silver, copper, cetylpyridinium chloride (CPC), fluoride and combinations thereof. One example of measuring fluorescence light is by way of confocal laser scanning microscopy.

Another aspect of the invention provides a kit comprising an EPS fluorescent probe; at least one ion fluorescent probe, alternatively two or more ion fluorescent probes; optionally instructions for use in dental biofilm. One advantage of the present method is that the ion and EPS probes fluoresce at different excitation/emission wavelength and as such co-localization of the probes in dental biofilm, especially the EPS, can be determined.

Yet another advantage is to simultaneously studying the role of two or more ions in the EPS area of dental biofilm to understand more complicated oral care formulations and/or complicated mechanisms of therapeutic action.

Yet another advantage of the present invention is the methods can be used to identify more efficacious oral care compositions as these compositions relate to ion delivery and/or efficacy in biofilm, especially in the EPS.

Yet another advantage of the present invention is the methods can be used to demonstrate, preferably visually demonstrate, to consumers or dental professionals how oral compositions work as these compositions relate to ion delivery in the EPS.

Yet another advantage of the present invention is avoiding the need of purifying EPS from dental biofilm.

Yet another advantage of the present invention is allowing the study of ions at varying depths of the EPS in the dental biofilm without damaging natural structure of biofilm.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
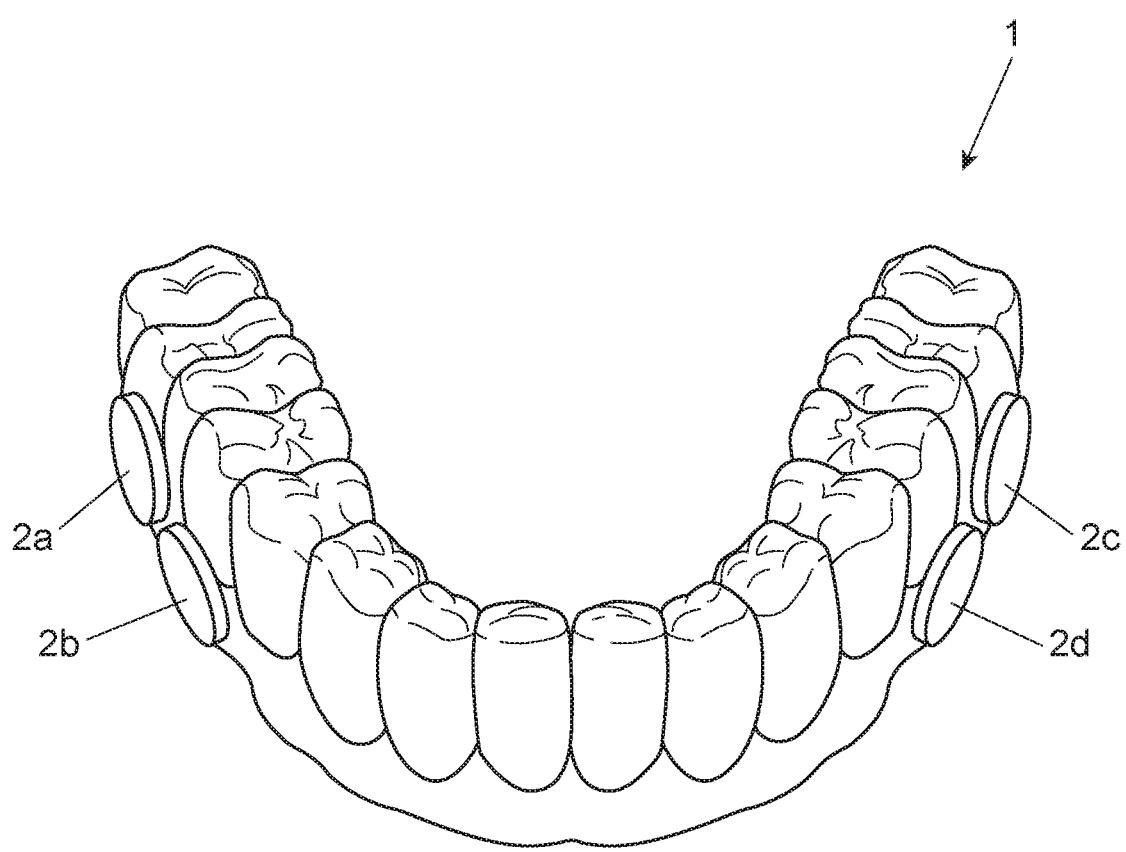
FIG. 1 is a perspective view of an oral splint with hydroxyapatite disks attached thereto.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

One aspect of the present disclosure is directed to a method of quantitating an ion within an extracellular polymer substances ("EPS") area of dental biofilm comprising the steps: optionally treating the dental biofilm with an oral care composition; labeling the treated dental biofilm with an EPS fluorescent probe; labeling the treated dental biofilm with an ion fluorescent probe; defining an EPS area of the dental biofilm by measuring fluorescent light emitted from the labeled EPS biofilm; and quantitating the ion by measuring fluorescence light emitted from the labeled ion within the defined EPS area of the biofilm. These steps need not be conducted in any specific order.

Treating the Biofilm with an Oral Care Composition

The term "biofilm" refers to the layer(s) of cells attached to a surface. A biofilm can be a bacterial biofilm that includes both alive and growing microbe cells as well as dead microbe cells. The biofilm can be composed of one cell type or it may be composed of two or more cell types, for example, a biofilm complex that is a multispecies bacterial community. A specific type of biofilm is "dental biofilm" (also known as "plaque biofilm," used herein interchangeably) which is biofilm that typically forms on tooth surfaces in the human mouth. Bacteria in a plaque biofilm have significantly different physiological characteristics, e.g. increased resistance to detergents and antibiotics, making biofilm research highly important. A non-limiting list of oral bacterial species is described at U.S. Pat. No. 6,309,835 B1, column 7, lines 12-30. These adherent microbe cells are frequently embedded within a self-produced matrix of extracellular polymeric substance (EPS). EPS are biopolymers of microbial origin in which biofilm microorganisms are embedded. *J. Bacteriol.* 2007, 189(22):7945. EPS is a polymeric conglomeration generally composed of calcium, extracellular DNA, glycoproteins, and polysaccharides. The biofilm may be either in vitro biofilm or in situ biofilm. Preferably the biofilm is in situ plaque biofilm because it more accurately reflects the conditions of the human mouth by providing a natural and undistributed biofilm. One approach that lends itself well to quantitating ions in the biofilm, especially in the EPS portion of the biofilm, over a defined period of time, is using in situ plaque biofilm.

Figure 2:
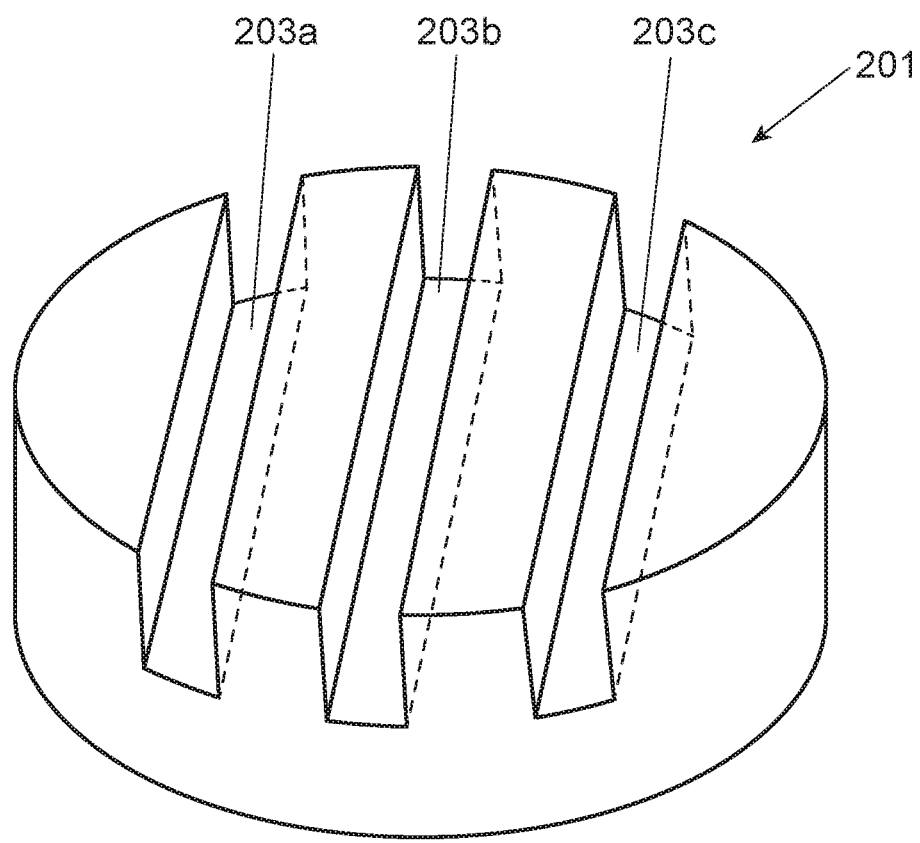
FIG. 2 is a perspective view of the hydroxyapatite disk having grooves therein.
Figure 3:
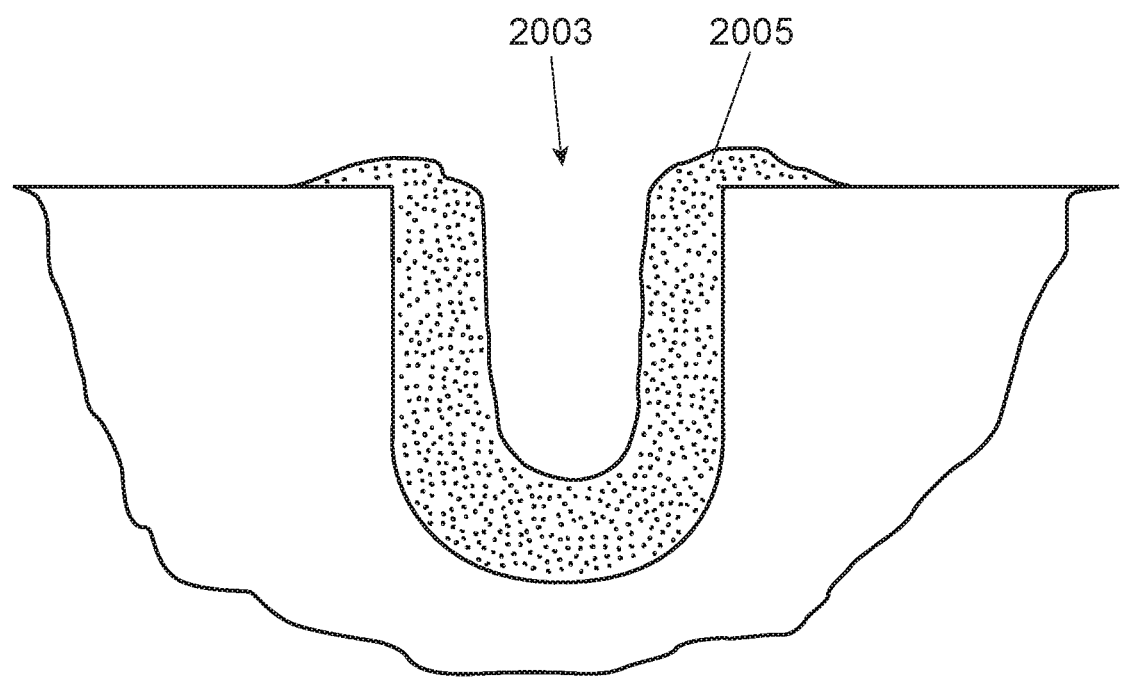
FIG. 3 is a schematic of a cross sectional view of the groove with biofilm therein.

A number of different surfaces for which the biofilm may attach are contemplated. These surfaces may include, for example, human enamel, bovine enamel, bovine dentine, hydroxyapatite, polished glass, and titanium. Considering the roughness of the surface of the substrate and its free energy are important factors for the in situ growth of plaque biofilm, enamel or hydroxyapatite are preferred surfaces to mimic a natural substrate for growth of plaque biofilm. On the other hand, due auto-fluorescence of enamel, hydroxyapatite is more preferred for the in situ growth of plaque biofilm. Hydroxyapatite, also called hydroxylapatite, ("HA") is a mineral form of calcium apatite generally having the formula $Ca_{10}(PO_4)_6(OH)_2$. In a particularly preferred approach, HA containing pieces (e.g., small disks) are used. These HA pieces are relatively small, preferably having an overall volume of 7 $mm^3$ to 110 $mm^3$, preferably from 25 $mm^3$ to 35 $mm^3$. The HA pieces are designed having a plurality of grooves (to allow plaque biofilm to attach inside the groove). For clarification, either in situ or in vitro plaque biofilm may be used to attach to the inside of the groove(s), but in situ plaque biofilm is preferred. The plurality of grooves preferably have dimensions that are from 50 um to 500 um deep and from 50 um to 500 um wide, more preferably from 100 um to 400 um deep and from 100 um to 400 um wide, even more preferably at least one of the grooves is from 250 um to 350 um deep and from 250 um to 350 um wide. Without wishing to be bound by theory, many human subjects do not care to have an oral appliance (containing these HA pieces) for more than two to three days. With grooves smaller than these dimensions, the groove is filled up with in situ plaque biofilm thereby not allowing the subject oral care composition and/or fluorescent probes to penetrate into the groove. On the other hand, if the dimensions of the groove are too large then the grooves do not lend themselves well to biofilm growth or attachment, particularly if the human subject is only going to wear the oral appliance for two to three days. In addition, these preferred groove dimensions provide for an optimum cross section view by conventional CLSM. In a specific example, and turning to FIG. 2, the HA disk (201) has three parallel grooves (203) (the two sides' grooves (203*a* and 203*c*) are 300 um wide and 300 um deep; while the middle grove (203*b*) (in between the two side grooves) is 500 um wide and 500 um deep). The middle groove is designed wider and deeper than the two sides' grooves so that the HA disk can be more easily separated into two identical half-disks for head-to-head comparison purposes. FIG. 3 is a schematic of a cross sectional view of the groove (2003) with biofilm (2005) therein.

Preferably the in situ plaque biofilm is attached to the surface of HA pieces as a result of the HA pieces being attached to an oral appliance (e.g., oral splint or mouthpiece) worn by human subjects for a defined period of time. This defined period of time is preferably from 6 hours to 4 days, more preferably from 1 day to 3 days, alternatively about 2 days. Accordingly, the method may comprise the step of having human subjects wearing the oral appliance for 6 hours to 4 days, preferably 1-3 days, more preferably 2 days; wherein at least a portion of the oral appliance comprises HA as a surface of the biofilm, and wherein the biofilm is an in situ plaque biofilm. The term "oral appliance" means a device that can be temporarily worn inside the oral cavity (i.e., mouth) of a human subject for up to multiple days at a time (but temporarily removed during eating or oral hygiene and the like). Non-limiting examples of an oral appliance include an oral splint, mouthpiece, and retainer. The oral appliance preferably has a plurality of HA containing pieces (e.g., small disks) releasably attached thereto. In other words, the human subject wears the oral appliance as to allow biofilm to attach/grow to the surfaces and grooves of the HA disk. After 6 hours to 4 days, preferably 2-3 days, more preferably 2 days, the HA disks are removed by the oral appliance that was worn by the human subject. FIG. 1 is an example of a splint (1) having a plurality of HA disks (2a, 2b, 2c, 2d) releasably attached to the splint. The splint (1) is worn over the teeth of a human subject (not shown) for a defined period of time with the objective of having biofilm grow/attach to the HA disks, preferably in grooves of the HA disks. In FIG. 1, the plurality of HA disks are on the interdental buccal side of the oral applicant. Although not shown in FIG. 1, a preferred location of the HA pieces is on the lingual side of the appliance. Without wishing to be bound by theory, the lingual side is even more difficult to brush thereby providing in situ plaque biofilm that is likely thicker (i.e., grows or forms more quickly than from other locations in the oral cavity). Moreover, there is also a suggestion that the in situ plaque biofilm resulting from the lingual side maybe by more toxic or pathogenic.

The biofilm may be treated with the oral care composition either in vivo or ex vivo. "In vivo" means that which takes place within the organism, specifically within the oral cavity of the human subject. For example, the human subject may wear an oral splint (and the HA disks releasably attached thereto) while using the oral care composition. "Ex vivo" means that which takes place outside an organism, specifically outside the oral cavity of the human subject. For example, after the splint is worn, the HA disks may be removed and then treated with the subject oral care composition. Such an ex vivo approach is preferable when assessing the penetration of ions in the biofilm or the amount of the ion deposition in the biofilm (e.g., single or multiple ion-containing product/composition usage).

The oral care composition may be any composition that is designed to be primarily used in the oral cavity in humans, preferably for the purpose of oral hygiene. The term "oral care composition" can be a single ingredient (e.g., an ion binder or ion source) or a formulation with multiple ingredients. The oral care composition may vary not only in ingredients but also in the concentration of these ingredients. Preferably these ingredient(s) are safe for use in the oral cavity of humans. Non-limiting examples of oral care compositions may include dentifrice, toothpaste, mouthwash, leave-on gel, etc. The term "ion binder" means displacing a specific ion by way of chelating, binding, removing, precipitating, or otherwise.

Oral care compositions may comprise a ion source or an ion binder to: (i) prevent or mitigate dental biofilm formation; (ii) disrupt existing dental biofilms; (iii) prevent or mitigate further dental biofilm growth; (iv) kill or attenuate particular organisms in the biofilm; or (v) combinations thereof. The oral care compositions may comprise more than one ion source or more than one ion binder or may comprise different combinations thereof.

The oral care composition may comprise an effective amount of an ion source. Preferably the ion source is selected from the group consisting of stannous, calcium, zinc, cetylpyridinium chloride, iron, silver, copper, fluoride, and combinations thereof. More preferably the ion source is a salt, preferably a water soluble salt.

In one example, the oral care compositions of the subject invention are those containing an ion source, such as one providing the following ions: stannous ($Sn^{2+}$), zinc ($Zn^{2+}$), fluoride ($F^-$), silver ($Ag^+$), copper ($Cu^{2+}$), Cetylpyridinium Chloride ($CPC^+$), and combinations thereof. A non-limiting example of an ion source ingredient used in stannous containing oral care compositions includes stannous fluoride. Such oral care compositions may typically contain from 0.0025% to 2%, by weight of the composition, of the ion source. In another example, the oral care composition comprises an ion binder. One example of an ion binder is sodium bicarbonate. Such oral care composition may typically contain from 0.0025% to 75%, by weight of the composition, of the ion binder.

In an alternative embodiment, the biofilm attaches to a test piece of mammalian (e.g., human or bovine) enamel surface. That is, pieces of enamel are subject to a relatively longer term study (e.g., 5-21 days). These pieces can also be releasably attached to an oral care appliance and worn by a human subject. This in situ method can be used to measure ion delivery and/or penetration and/or the effect of an oral care composition to ion bioavailability.

The method may comprise treating the biofilm with the oral care composition for a treatment contact time from: 1, 3, 5, 10, 30, or 45 seconds; or 1, 2, 3, 4, or 5 minutes; or 5, 10, 30, 60, 120 minutes; or 1 to 2 days; or 3 seconds to 48 hours; preferably from 1 minute to 3 minutes, or combinations thereof.

Labeling Biofilm with an EPS Fluorescent Probe

The biofilm is labeled with an EPS fluorescent probe. The method preferably further comprises the step of defining an EPS area of the biofilm by measuring fluorescent light emitted from the labeled EPS biofilm. In other words, the method is able to localize or spatially define the EPS within the biofilm. This measurement can be done with or without regard to fluorescence intensity. One preferred instrument in performing such measurements is confocal laser scanning microscopy (CLSM). As discussed in further detail below, preferably the method further comprises the step of quantitating the labeled ion(s) within the EPS defined area of the biofilm (i.e., co-localization).

"EPS fluorescent probe" means a fluorescent probe that specifically binds to EPS of a biofilm and emit fluorescence at a certain wavelength. One class of EPS fluorescent probes includes is a fluorescently labeled lectin. The term "fluorescently labeled lectin" is also inclusive of lectin derivatives. Non-limiting examples include Molecular Probes™ Concanavalin A™ (Con A) Conjugates, which selectively binds to α-mannopyranosyl and α-glucopyranosyl residues. One specific example is Concanavalin A™, Fluorescein Conjugate™, wherein excitation is 494 nm, and maximum light emission is detected at 518 nm. These EPS fluorescent probes are widely available as well as the procedure details in how to use them to quantitatively determine the location and/or amount of EPS.

Examples of an EPS fluorescent probe suitable for labeling the biofilm may be any one of the following compounds:
(a) Molecular Probes™ Concanavalin A™ Alexa Fluor® 350 Conjugate™;
(b) Molecular Probes™ Concanavalin A™ Alexa Fluor® 488 Conjugate™;
(c) Molecular Probes™ Concanavalin A™ Alexa Fluor® 594 Conjugate™;
(d) Molecular Probes™ Concanavalin A™ Alexa Fluor® 633 Conjugate™;

(e) Molecular Probes™ Concanavalin A™ Alexa Fluor® 647 Conjugate™;
(f) Molecular Probes™ Concanavalin A™ Fluorescein Conjugate™;
(g) Molecular Probes™ Concanavalin A™ Oregon Green® 488 Conjugate™;
(h) Molecular Probes™ Concanavalin A™ tetramethylrhodamine Conjugate™;
(i) Molecular Probes™ Concanavalin A™ Texas Red® Conjugate™.

One or more of these probes may be available from ThermoFisher Scientific Company, Waltham, Mass.

Labeling Biofilm with at Least One Ion Fluorescent Probe

The biofilm is labeled with one or more ion fluorescent probes. Preferably, the method further comprises the step of quantitating the ion by measuring the fluorescence light emitted from the labeled ion within the biofilm, preferably within the defined EPS area of the biofilm. Quantitating may also include assessing the intensity of fluorescence in a defined area of the biofilm. One preferred instrument in performing such quantification is confocal laser scanning microscopy (CLSM). Commercially available software is able to quantify fluorescence of the pixels from images taken. Three dimensional images can be constructed from a number of single images taken of the labeled calcium/biofilm.

"Ion fluorescent probe" means a fluorescent probe that specifically binds to one kind of ions and emit fluorescence at a certain wavelength. In recent years, significant emphasis has been placed on the development of new, highly selective fluorescent probes of ions because of their potential applications in biochemistry and environmental research. Many kinds of signaling mechanisms have been proposed and utilized for optical detection of ions, including photo-induced electron/energy transfer (PET), intramolecular charge transfer (ICT), fluorescence resonance energy transfer (FRET), and so on. Some of these fluorescent probes can also be applied in fluorescence bioimaging, which causes little cell damage and is highly sensitive with high-speed spatial analysis of living cells. Specifically, FRET imaging that affords simultaneous recording of two emission intensities at different wavelengths in the presence and absence of analytes has provided a facile method for visualizing complex biological processes at the molecular level. This technique appears to be suited to the study of physiological functions or pathogenesis of ions in biofilm and human body.

Non-limiting examples of a stannous fluorescent probe suitable for labeling the biofilm may include any one following of the compounds: (a) tert-butyl (3',6'-diamino-3-oxospiro[isoindoline-1,9'-xanthen]-2-yl)carbamate; (b) tert-butyl (3',6'-bis(dimethylamino)-3-oxospiro[isoindoline-1,9'-xanthen]-2-yl)carbamate; (c) tert-butyl (3',6'-bis(diethylamino)-3-oxospiro[isoindoline-1,9'-xanthen]-2-yl)carbamate; (d) tert-butyl (3',6'-bis(ethylamino)-2',7'-dimethyl-3-oxospiro[isoindoline-1,9'-xanthen]-2-yl)carbamate; (e) tert-butyl (3',6'-diamino-2',7'-dimethyl-3-oxospiro[isoindoline-1,9'-xanthen]-2-yl)carbamate; (f) tert-butyl (3-oxo-3',6'-di(pyrrolidin-1-yl)spiro[isoindoline-1,9'-xanthen]-2-yl)carbamate; (g) tert-butyl (3-oxo-3',6'-bis(phenylamino)spiro[isoindoline-1,9'-xanthen]-2-yl)carbamate; (h) tert-butyl (3-oxo-3',6'-di(piperidin-1-yl)spiro[isoindoline-1,9'-xanthen]-2-yl)carbamate; (i) tert-butyl (3',6'-dimorpholino-3-oxospiro[isoindoline-1,9'-xanthen]-2-yl)carbamate; (j) tert-butyl(2',7'-dibutyl-3',6'-bis(diethylamino)-3-oxospiro[isoindoline-1,9'-xanthen]-2-yl)carbamate; (k) tert-butyl (2',7'-dimethyl-3-oxo-3',6'-di(piperidin-1-yl)spiro[isoindoline-1,9'-xanthen]-2-yl)carbamate; (l) tert-butyl (3-oxo-1',2',3',4',10',11',12',13'-octahydrospiro[isoindoline-1,7'-pyrano[2,3-f:6,5-f']diquinolin]-2-yl)carbamate; (m) tert-butyl (3-oxo-1',2',3',4',8',9',10',11'-octahydrospiro[isoindoline-1,6'-pyrano[3,2-g:5,6-g']diquinolin]-2-yl)carbamate; (n) N-(3',6'-bis(diethylamino)-3-oxospiro[isoindoline-1,9'-xanthen]-2-yl)propionamide; (p) N-(3',6'-bis(diethylamino)-3-oxospiro[isoindoline-1,9'-xanthen]-2-yl)butyramide; and (q) N-(3',6'-bis(diethylamino)-3-oxospiro[isoindoline-1,9'-xanthen]-2-yl)pentanamide. Preferably the stannous probe is selected from: N-(3',6'-bis(diethylamino)-3-oxospiro[isoindoline-1,9'-xanthen]-2-yl)propionamide; N-(3',6'-bis(diethylamino)-3-oxospiro[isoindoline-1,9'-xanthen]-2-yl)butyramide; and N-(3',6'-bis(diethylamino)-3-oxospiro[isoindoline-1,9'-xanthen]-2-yl)pentanamide. Generally these stannous fluorescent probes contain a Rhodamine B derivative moiety as fluorophore, linked via amide moiety to a carbazate group. Further details are described in the WO 2015/139577 A1 (24 Sep. 2015) or US equivalent publication thereof. One or more of these probes may be available from Dr. Tao Yi, Department of Chemistry, Fudan University, Shanghai, China.

Examples of a zinc fluorescent probe suitable for labeling the biofilm may include any one or more of following compounds:
(a) Zinquin ethyl ester, from Sigma-Aldrich; and
(b) TSQ [N-(6-Methoxy-8-quinolyl)-p-toluenesulfonamide], from AAT Bioquest Inc.

Examples of an iron fluorescent probe suitable for labeling the biofilm may include any one following of the compounds:
(a) 2-(2-(((1H-pyrrol-2-yl)methyl)amino)ethyl)-3',6'-diaminospiro[isoindoline-1,9'-xanthen]-3-on, as described in CN103913441BB;
(b) 2-(3-((2-methylquinolin-8-yl)oxy)propyl)isoindoline-1,3-dione, described in Org. Biomol. Chem., 2012, 10, 9634;
(c) 8-(3-(1,3-dioxoisoindolin-2-yl)propoxy)quinoline-2-carbaldehyde, also described in Org. Biomol. Chem., 2012, 10, 9634; and
(d) Rhodamine-based fluorescent probe for iron ion as described in Talanta 80 (2010) 2093-2098.

Examples of a copper fluorescent probe suitable for labeling the biofilm may include any one following of the compounds:
(a) 2-[bis(2-hydroxyamino-2-oxoethyl)amino]-3-[2-(1-ethyl-3,3-dimathylidolin-2-ylidene) cyclohex-1-enyl]vinyl-1-ethyl-3,3-dimethyl-3H-indolium, as described in Chemical Communications, 2011, 47(27):7755-7757;
(b) so called "FluTPA1" and "FluTPA2", described in Journal of the American Chemical Society, 2010, 132(17):5938;
(c) monoboronic acid-conjugated rhodamine probe, described in Chemical Communications, 2009, 45(45): 5915-5917; and
(d) rhodamine B derivative colorimetric and fluorescent sensor (synthesized by condensation reaction of rhodamine B hydrazide and 2,4-dihydroxybenzaldehyde), described in Sensors & Actuators B Chemical, 2011, 156(2):546-552.

Examples of a calcium fluorescent probe suitable for labeling the biofilm may include any one following of the compounds:
(a) Fluo-3™, AM™, cell permeant fluorescence stains;
(b) Fluo-3™, Pentapotassium Salt, cell impermeant fluorescence stains;
(c) Fluo-4™, AM™, cell permeant fluorescence stains;
(d) Fluo-4™, Pentapotassium Salt, cell impermeant fluorescence stains;

(e) Fluo-4 Direct™ Calcium Assay Kit;
(f) Mag-Fluo-4™, Tetrapotassium Salt, cell impermeant fluorescence stains; and
(g) Fluo-5F™, AM™, cell permeant fluorescence stains;
One or more of these probes may be available from ThermoFisher Scientific Company, Waltham, Mass.

The subject biofilm is generally incubated with the ion probe in dark for 15-60 minutes, preferably 30 minutes and excitation light is provided to the incubated biofilm at a wavelength according to instruction manuals of ion probes or relevant literature/patent references. The wavelength of light emission detection as well as the procedure details in how to use ion probes are determined according to these manuals and references.

Defining an EPS Area of the Dental Biofilm and/or Quantitating the Labeled EPS

The method of the present invention comprising the step of defining an EPS area of the dental biofilm (and/or quantitating the labeled EPS) by measuring fluorescence light emitted from the labeled EPS. One preferred instrument in performing such quantification is confocal laser scanning microscopy (CLSM). Commercially available software is able to quantify pixels from the images taken of the fluorescent labeled EPS. Three dimensional images can be constructed from a number of single images taken of the labeled EPS.

Quantitating the Labeled Ion

The method of the present invention comprising the step of quantitating the ion by measuring fluorescence light emitted from the labeled ion within the defined EPS area of the biofilm. Similarly, a preferred instrument in performing such quantification is confocal laser scanning microscopy (CLSM) including the commercially available software.

Optionally Using Two or More Ion Fluorescent Probes

The method of the present invention may optionally comprise the step of labeling the treated dental biofilm with at least two ion fluorescent probes, alternatively three or more ion fluorescent probes. When a plurality of ion fluorescent probes are used, each ion's penetration/distribution is visualized and quantified within the defined EPS area of the biofilm via the EPS fluorescent probes. This allows for oral care composition formulary guidance based upon any desirably binding and/or distribution patterns assessed. For example, and without wishing to be bound by theory, compositions containing both Zn and Sn ion sources, the use of these ion and EPS fluorescent probes would allow an understanding for the ratios of each ion to be assessed for depth of penetration. The method can further be used to assess for antimicrobial effects (e.g., lipopolysaccharides binding or bactericide) through the use of other probes. The ability for multiple channels (i.e., different fluorescent wavelengths and color range) to be used by CLSM allows the overlay and measure of multiple ion/EPS probes.

EXAMPLES

Data is provided on the fluorescence intensity ratio and spatial co-localization percentage of stannous/EPS in biofilm for a stannous containing toothpaste, a non-stannous containing toothpaste, and a negative control. Methodology is first described.

The substrate for biofilm growth is described. Hydroxyapatite ("HA") disks are used for in situ growth of biofilm. The HA disks are designed having three parallel grooves (300 um wide, 300 um deep for two sides' grooves, while 500 um wide, 500 um deep for the middle groove) in each disk. When attaching disks to subject's mouth, keeping these grooves vertical, to mimic interproximal gap between teeth, the hard-to-clean area where plaque accumulates, this model allows the collection of undisturbed naturally grown dental plaque biofilm from the grooves. HA disks are manufactured by Shanghai Bei'erkang biomedicine limited company.

Human subjects wearing a splint are described. Each subject wears up to 12 HA disks on the splint to make sure at least 9 HA disks are available after 48 hours. A non-limiting example of such a splint and HA disks are shown in FIG. 1. The device (1) holds a plurality of HA disks (2a-2d). Although not shown in FIG. 1, the disks can be positioned such that the recede in the inter-dental space between the teeth (since this location is prone to plaque (given the difficulty in cleaning etc.)). The subjects withdraw the splint (the splint stored in an opaque container under humid conditions) only during meals and to perform oral hygiene procedures. Immediately thereafter, the splint is worn again. Subjects are asked to use a straw when drinking.

The procedure for in situ biofilm release from HA disk is described. All HA disks are removed from the splint at 48 hours by tweezers. Tweezers are used to hold the edge of HA disk and transfer the HA disk to a 2 ml centrifuge tube containing PBS (phosphate buffered saline) solution. Tweezers are washed thoroughly (water; 75% alcohol; and then deionized water) before every disk transfer.

The preparation for Phosphate Buffer Saline solution is described. One phosphate buffer saline tablet (available from Sigma-Aldrich Corp., MO, USA) is added to 200 grams deionized water in a 250 ml beaker. After stirring thoroughly, the solution is stored at 4° C. for up to 30 days before usage.

The preparation for toothpaste supernatant is described. 15 grams of deionized water is added to 5 grams toothpaste in a 100 ml beaker. After stirring thoroughly, the mixture is centrifuge 11,000×g for 20 minutes. The supernatant is prepared immediately before usage or at most one day before usage and stored at 4° C.

After the HA disks are removed from the splint, the HA disks are used for ex vivo treatment by different oral care compositions. After being treated with the subject supernatant and labeled with EPS fluorescent probe and stannous fluorescent probe, the biofilm in the grooves is measured by confocal laser scanning microscopy (CLSM).

Disk preparation is described. The HA disks are rinsed in PBS solution and each HA disk is divided into two halves by tweezers. Thereafter each half-disk specimen is placed into 500-1000 ul of PBS solution statically for 1 minute. Each specimen is treated for two minutes by either PBS solution or toothpaste supernatant. Each specimen is washed by holding each disk with tweezers, shaken for ten rounds of back and forth in 1 ml of PBS solution. This washing cycle is repeated. Thereafter each specimen is immersed into 500-1000 ul PBS solution statically for 5 minutes.

Fluorescence staining and microscopy is described. It is reported that the Molecular Probes™ Concanavalin A™ Conjugates is a reliable fluorescent labeled lectin when assessing EPS in a natural plaque biofilm, which is rich of multiple types of glycoproteins. Lectins are versatile probes for detecting glycoconjugates in histochemical and flow cytometric applications and for localizing glycoproteins in biofilms. Concanavalin A selectively binds to α-mannopyranosyl and α-glucopyranosyl residues. In neutral and alkaline solutions, concanavalin A exists as a tetramer with a molecular weight of approximately 104,000 daltons. In acidic solutions (e.g., pH below 5.0), concanavalin A exists as a dimer. Sn probe selectively binds to stannous ions and emits fluorescence in red channel. Both the Con-A and Sn probes exert linear correlation between the emission fluorescence intensity and the glycoprotein and stannous concentration respectively, which indicate that the fluorescence intensity increased as a linear function of glycoprotein and stannous concentration respectively.

After treatment and immersing, each half-disk specimen is stained with a dye mixture solution of the Sn probe together with Molecular Probes™ Concanavalin A™, Fluorescein Conjugate™ probe (containing 5 uM Sn probe+5 uM Con-A probe) for 30 minutes in the dark. After staining, each disk is immersed into 500-1000 ul PBS solution statically for 2 minutes. The disks are washed again, by holding each disk with tweezers, shaken for five rounds of back and forth in 1 ml PBS solution, and repeated. For Sn/EPS dye stained samples, the following parameters are used: $\lambda ex$=488 nm/543 nm respectively, $\lambda em$=500/580 nm respectively, 20× objective lens, and scanning from bottom of surface bacteria for 60 um depth with step size of 3 um. Although not shown, the other half-disk can be stained with L7012 LIVE/DEAD® dye solution as a control (containing 5 uM Syto-9+30 uM propidium iodide) for 15 minutes in the dark. For the L7012 LIVE/DEAD® dyed stained sample, the following parameters are used: $\lambda ex$=488 nm, $\lambda em$=500/635 nm respectively, 20× objective lens, and scanning from bottom of surface bacteria for 60 um with step size of 3 um.

Confocal Laser Scanning Microscopy (CLSM) is described. The Leica™ TCS SP8 AOBS spectral confocal microscope (available from Leica Mikroskopie GmbH, Wetzlar, Germany) is used. The confocal system consists of a Leica™ DM6000B upright microscope and a Leica™ DMIRE2 inverted microscope. An upright stand is used for applications involving slide-mounted specimens; whereas the inverted stand, having a 37° C. incubation chamber and $CO_2$ enrichment accessories, provides for live cell applications. The microscopes share an exchangeable laser scan head and, in addition to their own electromotor-driven stages, a galvanometer-driven high precision Z-stage which facilitates rapid imaging in the focal (Z) plane. In addition to epifluorescence, the microscopes support a variety of transmitted light contrast methods including bright field, polarizing light and differential interference contrast, and are equipped with 5×, 20×, 40×, 63× (oil and dry) and 100× (oil) Leica™ objective lenses.

The laser scanning and detection system is described. The TCS SP8 AOBS confocal laser scanning system (available from Leica Lasertechnik GmbH, Heidelberg, Germany) is supplied with four lasers (one diode, one argon, and two helium neon lasers) thus allowing excitation of a broad range of fluorochromes within the UV, visible and far red ranges of the electromagnetic spectrum. The design of the laser scan head, which incorporates acousto-optical tunable filters (AOTF), an acousto-optical beam splitter (AOBS) and four prism spectrophotometer detectors, permits simultaneous excitation and detection of three fluorochromes. The upright microscope also has a transmission light detector making it possible to overlay a transmitted light image upon a fluorescence recording.

Leica™ Confocal software LAS AF3.3.0 is used. The confocal is controlled via a standard Pentium PC equipped with dual monitors and running Leica™ Confocal Software LAS AF3.3.0 (available from Leica Lasertechnik GmbH, Heidelberg, Germany). The Leica Confocal Software LAS AF3.3.0 provides an interface for multi-dimensional image series acquisition, processing and analysis, that includes 3D reconstruction and measurement, physiological recording and analysis, time-lapse, fluorochrome co-localization, photo-bleaching techniques such as FRAP and FRET, spectral immixing and multicolour restoration. Regarding image analysis of the Sn probe/Con-A probe co-stained samples, fluorescence intensity ratio of red pixels (labeled stannous) to green pixels (labeled EPS) are quantified. The co-localization percentage of red pixels (labeled stannous) overlapping with green pixels (labeled EPS) is also measured.

Turning to Table 1, the fluorescence intensity ratio of Sn/EPS within in situ plaque biofilm is provided for one stannous containing toothpaste, one non-stannous containing toothpaste and a negative control. The procedures previously described are used. The biofilm is treated with the subject oral care compositions first, and then the treated biofilm is labeled with the Con-A and stannous probes. Using software, the mean fluorescence intensities of red pixels (staining stannous ions) and green pixels (staining EPS) are given, and then the fluorescence intensity ratio of red pixels to green pixels is calculated as the relative stannous concentration normalized with EPS amount. Also, the pixel overlap of "green pixels" (from EPS fluorescent probe) and that of "red pixels" (from stannous fluorescent probe) are identified, and then this value is divided by all non-black pixels (that includes non-overlapping red and/or green pixels) to provide a co-localization percentage of stannous ions in the defined EPS area.

In Table 1, data is presented from assessing following oral compositions: two commercially available toothpaste products are: CREST® PRO-HEALTH™ (LOT #5058GR, with 0.454 wt % stannous fluoride) ("CPH") as the stannous containing toothpaste; CREST® CAVITY PROTECTION™ (LOT #42891864AD, with 0.243 wt % sodium fluoride) ("CCP") as the non-stannous containing toothpaste. Phosphate buffer saline solution ("PBS") is used as the negative control. The results show that CPH shows significantly higher Sn/EPS fluorescence ratio and higher co-localization percentage than CCP and PBS. There is no significant difference between CCP and PBS treatments. This is consistent with both bactericidal efficacy comparison and plaque prevention efficacy comparison in a clinical 4-day plaque result (unpublished).

TABLE 1

Stannous to EPS fluorescence ratio and co-localization percentage of stannous within a defined EPS area.

|  | Stannous to EPS fluorescence ratio (mean ± SD) | Co-localization percentage (%) of stannous within a defined EPS area (mean ± SD) |
| --- | --- | --- |
| PBS | 0.11 ± 0.03 | 7.56 ± 1.20 |
| CCP | 0.13 ± 0.02 | 8.21 ± 1.75 |
| CPH | 7.56 ± 0.88 | 87.50 ± 7.35 |

An example of using EPS probe with two ion probes is described. The procedures previously described are used. The biofilm is treated with the subject oral care compositions first, and then the treated biofilm is labeled with three probes for 30 min in dark: (1) an EPS probe, Molecular Probes™ Concanavalin A™ Alexa Fluor® 350 Conjugate™; (2) a stannous probe, which is described in the WO 2015/139577 A1 (24 Sep. 2015) or US equivalent publication thereof, available from Dr. Tao Yi, Department of Chemistry, Fudan University, Shanghai, China; (3) a zinc probe, which can be obtained from Dr. Tao Yi, Department of Chemistry, Fudan University, Shanghai, China. The following parameters for EPS probe, stannous probe and zinc probe are used: $\lambda ex$=346/488 nm/543 nm respectively, $\lambda em$=442/520/580 nm respectively, 20× objective lens, and scanning from bottom of surface bacteria for 60 um depth with step size of 3 um. CLSM images are obtained with Leica™ TCS SP8 AOBS spectral confocal microscope and Leica™ Confocal software LAS AF3.3.0.

Figure 4:
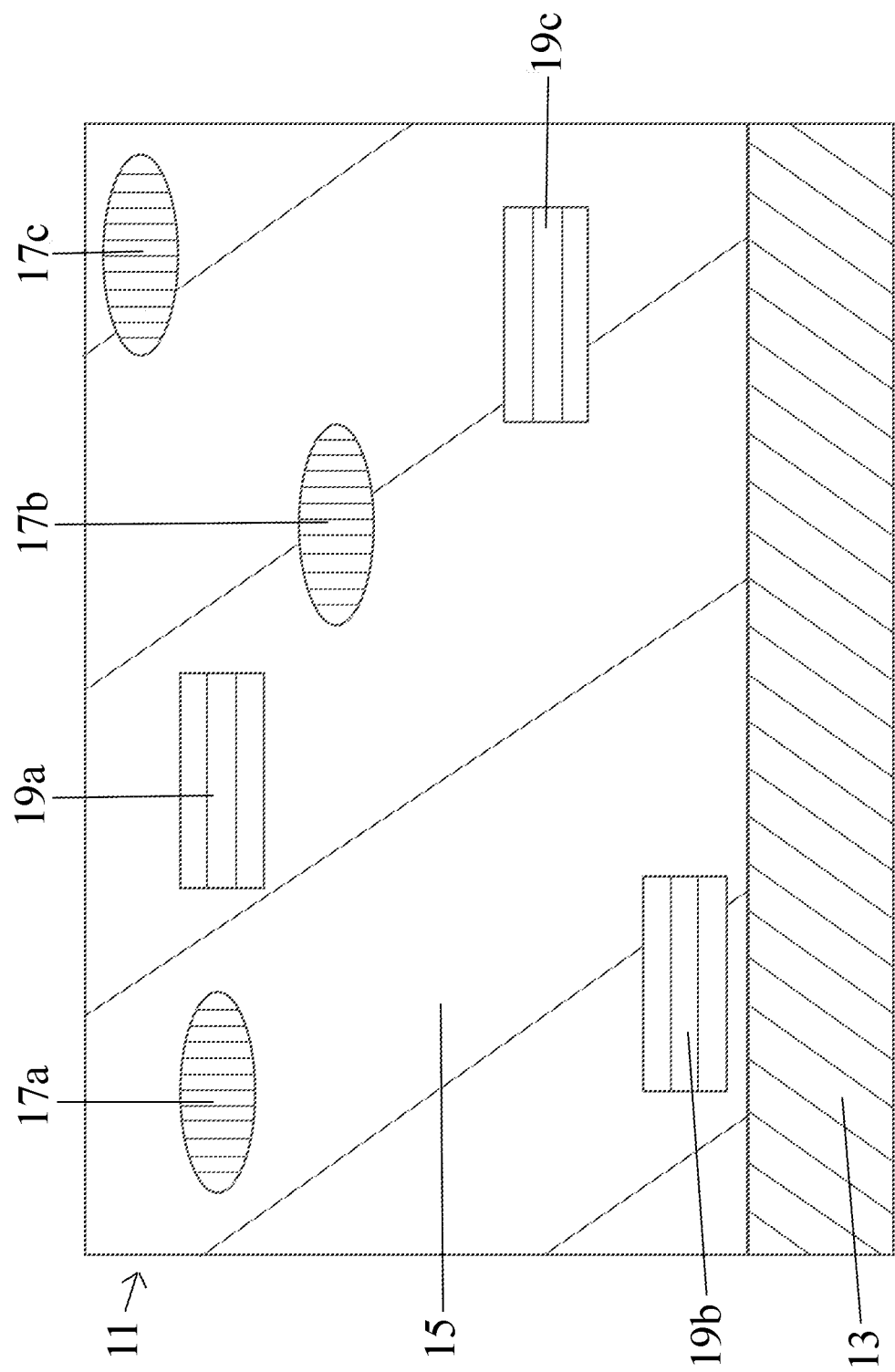
FIG. 4 is a dramatization of a cross sectional view of fluorescent-labeled stannous and zinc overlapping with fluorescent-labeled EPS of a biofilm.

Turning to FIG. 4, a dramatization is made showing what is observed by CLSM images (as a cross section). The biofilm is treated with CPH toothpaste supernatant for two minutes, and the treated biofilm is then co-labeled with EPS fluorescent probe, a zinc fluorescent probe, and a stannous fluorescent probe. Thereafter, the biofilm is observed by CLSM. The sample (11) contains an EPS area (15) of biofilm adhered to the HA disk (13). The EPS area (15) is defined by measuring a blue fluorescent light emitted from the labeled EPS biofilm. Zinc (17a, 17b, 17c) is quantified by measuring the green fluorescent light emitted from the labeled zinc ion (within the defined EPS area (15)). Stannous (19a, 19b, 19c) is quantified by measuring the red fluorescent light emitted from the labeled stannous ion. The data that indicates stannous penetrates deeper into the biofilm (i.e., nearer the HAP disk (13)) than zinc because of the localization of some of the stannous ions (e.g., 19b) in closer proximity to the HA disk (13).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of quantitating an ion selected from the group consisting of calcium, stannous, zinc, silver, copper, cetylpyridinium chloride, fluoride, and combinations thereof in a defined extracellular polymer substance ("EPS") area of dental biofilm comprising the steps:
   (a) treating the dental biofilm with an oral care composition comprising an ion source selected from the group consisting of stannous, calcium, zinc, cetylpyridinium chloride, silver, copper, fluoride, and combinations thereof;
   (b) labeling the treated dental biofilm with an EPS fluorescent probe;
   (c) labeling the treated dental biofilm with at least one ion fluorescent probe;
   (d) defining the EPS area of the dental biofilm by measuring fluorescent light emitted from the labeled EPS biofilm; and
   (e) quantitating the ion by measuring fluorescence light emitted from the labeled ion within the defined EPS area of the biofilm.

2. The method of claim 1, wherein the dental biofilm is treated with the oral care composition for a treatment contact time from 3 seconds to 48 hours.

3. The method of claim 2, wherein the treatment contact time is from 1 minute to 3 minutes, and wherein the oral care composition is selected from the group consisting of dentifrice, toothpaste, leave-on gel, gel, mouthwash, and combinations thereof.

4. The method of claim 1, wherein the ion source is a water soluble salt.

5. The method of claim 1, wherein the ion source is a stannous salt.

6. The method of claim 5, wherein the ion fluorescent probe is a stannous fluorescent probe.

7. The method of claim 1, wherein the ion source is a calcium salt.

8. The method of claim 7, wherein the ion fluorescent probe is a calcium fluorescent probe.

9. The method of claim 1, wherein the oral care composition comprises an effective amount of an ion binder.

10. The method of claim 9, wherein the ion fluorescent probe is a calcium fluorescent probe.

11. The method of claim 1, wherein the ion source is a zinc salt, and wherein the ion fluorescent probe is a zinc fluorescent probe.

12. The method of claim 1, wherein the steps of labeling the biofilm with the EPS fluorescent probe and the ion fluorescent probe are conducted before the step of treating the biofilm with the oral care composition; and wherein the step of measuring fluorescence light is by confocal laser scanning microscopy (CLSM).

13. The method of claim 1, further comprising the step of having human subjects wear an oral appliance for 6 hours to 4 days, wherein at least a portion of the oral appliance comprises hydroxyapatite (HA) as a surface of the biofilm, wherein the biofilm is an in situ plaque biofilm.

14. The method of claim 13, wherein the in situ biofilm on the HA surface is treated with the oral care composition either ex vivo or in vivo.

15. The method of claim 14, wherein the portion of the oral appliance comprising HA further comprises a plurality of grooves, wherein an inside surface of the groove is said surface of the in situ biofilm, wherein at least one groove is 250 microns to 350 microns deep and from 250 microns to 350 microns wide.

16. The method of claim 1, wherein the EPS fluorescent probe is a fluorescently labeled lectin.

17. The method according of claim 1, wherein the step of labeling the treated dental biofilm is with at least two ion fluorescent probes.

* * * * *